(12) United States Patent
Hanifpour et al.

(10) Patent No.: US 11,505,626 B2
(45) Date of Patent: Nov. 22, 2022

(54) PROCESS FOR THE PRODUCTION OF END-SATURATED POLYALFAOLEFIN LUBRICANTS

(71) Applicants: IRAN POLYMER AND PETROCHEMICAL INSTITUTE, Tehran (IR); UNIVERSITAT DE GIRONA, Girona (ES)

(72) Inventors: Ahad Hanifpour, Tehran (IR); Naeimeh Bahri-Laleh, Tehran (IR); Mehdi Nekoomanesh, Tehran (IR); Albert Poater, Girona (ES)

(73) Assignees: IRAN POLYMER AND PETROCHEMICAL INSTITUTE, Tehran (IR); UNIVERSITAT DE GIRONA, Girona (ES)

(*) Notice: Subject to any disclaimer, the term of this patent is extended or adjusted under 35 U.S.C. 154(b) by 0 days.

(21) Appl. No.: 17/217,493

(22) Filed: Mar. 30, 2021

(65) Prior Publication Data

US 2022/0315674 A1 Oct. 6, 2022

(51) Int. Cl.
| | | |
|---|---|---|
| C08F 4/64 | (2006.01) | |
| C08F 4/646 | (2006.01) | |
| C08F 110/14 | (2006.01) | |
| C10M 107/10 | (2006.01) | |
| C07F 7/28 | (2006.01) | |
| C07C 213/08 | (2006.01) | |
| C10M 177/00 | (2006.01) | |
| C10N 70/00 | (2006.01) | |

(52) U.S. Cl.
CPC ............ *C08F 4/646* (2013.01); *C07C 213/08* (2013.01); *C07F 7/28* (2013.01); *C08F 110/14* (2013.01); *C10M 107/10* (2013.01); *C10M 177/00* (2013.01); *C10M 2205/0285* (2013.01); *C10N 2070/00* (2013.01)

(58) Field of Classification Search
CPC ..... C08F 4/646; C08F 110/14; C10M 107/10; C10M 177/00; C10M 2205/0285; C10N 2070/00
See application file for complete search history.

(56) References Cited

U.S. PATENT DOCUMENTS

| | | | |
|---|---|---|---|
| 2011/0178348 A1* | 7/2011 | Heilman | C07C 9/22 585/16 |
| 2014/0039137 A1* | 2/2014 | Giesbrecht | C08F 10/00 526/133 |

(Continued)

OTHER PUBLICATIONS

Zhang et al., "Preparation, characterization and tribological properties of polyalphaolefin with magnetic reduced graphene oxide/Fe3O4", Tribology International, Elsevier, vol. 141, 2020, 105952, 10 pages.

(Continued)

*Primary Examiner* — Ellen M McAvoy
(74) *Attorney, Agent, or Firm* — Hayes Soloway PC

(57) ABSTRACT

This invention relates to novel and improved catalyst and catalysts systems for the oligomerization of the higher olefins, which produce lubricants having improved properties, such as end-saturated oligomer chains which are needless to hydrogenation process, low kinematic viscosity and/or high viscosity index, low pour point, and high flash point lubricants.

4 Claims, 6 Drawing Sheets

(56) References Cited

U.S. PATENT DOCUMENTS

2015/0158958 A1* 6/2015 Harrington ......... C08F 4/64189
526/144
2020/0165362 A1* 5/2020 Bae ..................... C08F 10/14
2020/0207688 A1* 7/2020 Kim ..................... C10M 107/10

OTHER PUBLICATIONS

Biresaw, "Biobased Polyalphaolefin Base Oil: Chemical, Physical, and Tribological Properties" Springer, Tribology Letters, vol. 66, Issue 76, 2018, 16 pages.

* cited by examiner

PROCESS FOR THE PRODUCTION OF END-SATURATED POLYALFAOLEFIN LUBRICANTS

This invention relates to novel and improved catalyst and catalysts systems for the oligomerization of the higher olefins, which produce lubricants having improved properties, such as end-saturated oligomer chains which are needless to hydrogenation process, low kinematic viscosity and/or high viscosity index, low pour point, and high flash point lubricants.

BACKGROUND ART

To reduce global energy consumption, automobile engines are expected to be energy efficient. Low-viscosity lubricants can effectively reduce friction loss in engines, thereby making them energy efficient. One of the major lubricant families used in automobile industry to reach the so-called goal is PAO type lubricants. Polyalphaolefins (PAOs), the hydrogenated α-olefin oligomers of linear α-olefins (primarily $C_8$-$C_{12}$), that belong to the group IV of API category, are synthetic oils used as base oils in high-performance engine lubricants. Base oils play a major role in determining a lubricant's performance. PAOs have all hydrocarbon structure, without double bonds, ring structures, S and N containing components or waxy hydrocarbons. The non-polar nature of PAOs, together with their high viscosity index (VI, >130), good oxidation stability, low pour point and good compatibility with mineral oils make them prominent candidates in engine oil topic, at both low and high temperature applications (Biresaw G, 2018, Biobased Polyalphaolefin Base Oil: Chemical, Physical, and Tribological Properties. Tribol Lett 66: 76).

Although a varied array of Lewis acid catalysts including coordination catalysts, Lewis acid catalysts, liquid coordination complexes, and ionic liquid is reported for the synthesis of PAOs, the industrial process is still dominated by BFs-donor to obtain the low viscosity grade PAO lubricants (2-10 cSt) (Zhang Q, Wu B, Song R, Song H, Zhang J, Hu X, 2020, Preparation, characterization and tribological properties of polyalphaolefin with magnetic reduced graphene oxide/$Fe_3O_4$. Tribol Int 141: 105952).

Because of the extremely high hazardousness and corrosiveness of $BF_3$, some efforts have still been in progress to decrease kinematic viscosity and increase VI of the PAO oligomers by using new catalyst systems. Accordingly, there is a need in the art for new and improved catalyst systems/oligomerization techniques for the oligomerization of higher olefins for one or more of the following purposes: to increase catalytic activity and/or to achieve one or more specific lubricant properties, such as end-saturated polyolefin chains, low kinematic viscosity (KV) and/or high viscosity index (VI), low pour point and also high flash point lubricants.

Furthermore, the industrial process currently used to achieve PAOs, involves a 3-stages process consisting of oligomerization, hydrogenation and distillation, to separate the 1-decene oligomers and blending the components in required ratios to obtain the different grades of PAOs. In fact, not everything is an advantage for crude PAOs, as they involve living with the existence of carbon-carbon double bonds, which are susceptible to the oxidation at high temperatures. To solve this issue, the hydrofinishing process is applied that simply consists of the complete saturation of the oligomeric chains by means of the introduction of molecular hydrogen at high pressure and temperature (>30 bar and >200° C.). This extremely increases the risk and cost of PAO production.

In our suggested process, a new method is introduced to achieve fully hydrogenated low viscosity PAO in a single reactor. This process not only decreases the hazardousness and corrosiveness of current industrially employed $BF_3$ catalyst technology, but also resolves the high risk of PAO production by the elimination of hydrogenation step.

SUMMARY OF THE INVENTION

The present invention discloses a novel catalyst system and an efficient method for the oligomerization of the α-olefins to produce saturated polyalphaolefins (PAOs) thorough chain coordination transfer oligomerization (CCTO) technique. Via this new method, saturated PAO is produced in a single reactor without hydrogenation process.

Summarizing the technology, the catalyst system of the invention and the olefin oligomerization method can produce a range of low viscosity saturated PAOs (from PAO4 to PAO8), which are needless of hydrogenation stage. It extremely diminishes PAO synthesis cost and risk, since for the hydrogenation of commercial PAOs via the current technologies, a hydrogenation step which operates at high $H_2$ pressure (more than 30 bar) and temperature (higher than 200° C.) is required.

Therefore, a first aspect of the present invention related to a novel catalyst compound of formula:

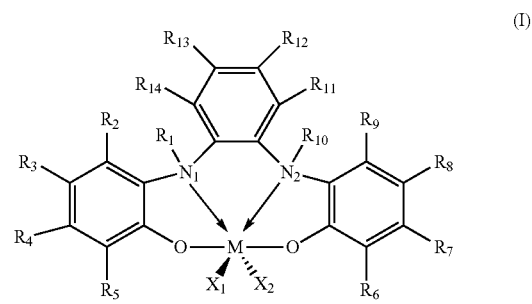

(I)

wherein M is selected from titanium (Ti), zirconium (Zr), hafnium (Hf), and rutherfordium (Rf);

$X_1$ and $X_2$ are independently selected from a $C_1$ to $C_{20}$ hydrocarbyl radical and halogen, or $X_1$ and $X_2$ join together to form a $C_4$ to $C_{12}$ cyclic or polycyclic ring structure, provided, with the proviso that wherein M is trivalent metal then $X_2$ is not present;

$R_1$, $R_2$, $R_4$, $R_7$, $R_9$, $R_{10}$, $R_{11}$, $R_{12}$, $R_{13}$, and $R_{14}$ are independently selected from a hydrogen and a $C_1$ to $C_{10}$ hydrocarbyl group; and $R_3$, $R_5$, $R_6$, and $R_3$ are independently a $C_1$ to $C_{40}$ hydrocarbyl group.

In a preferred embodiment, M is titanium.

In another preferred embodiment, $X_1$ and $X_2$ are halogen, and more preferred are chlorine.

In another preferred embodiment, $R_1$, $R_2$, $R_4$, $R_7$, $R_9$, $R_{10}$, $R_{11}$, and $R_{14}$ are hydrogen, therefore the catalyst compound is of formula:

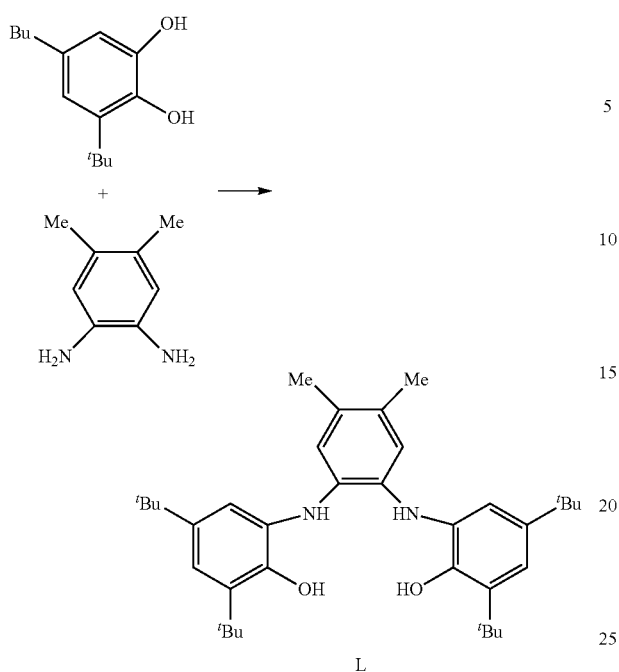

L wherein M, $X_1$, $X_2$, $R_3$, $R_5$, $R_6$, $R_3$, $R_{12}$, and $R_{13}$ are defined as above.

In another preferred embodiment, $R_3$, $R_5$, $R_6$, $R_3$, $R_{12}$, and $R_{13}$ are independently selected from a $C_1$ to $C_{20}$ hydrocarbyl radical; more preferably $R_3$, $R_5$, $R_6$, $R_3$, $R_{12}$, and $R_{13}$ are independently selected from a $C_1$-$C_{10}$ alkyl; more preferably $R_3$, $R_5$, $R_6$, $R_3$, $R_{12}$, and $R_{13}$ are independently selected from methyl, ethyl, propyl, butyl, and tert-butyl.

In another preferred embodiment, the catalyst compound is symmetrical.

In another preferred embodiment, the catalyst compound is a compound of formula:

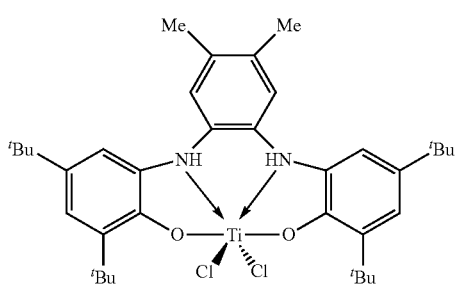

In another embodiment, the invention relates to a catalyst system comprising a) amino bis-phenolate-containing group IV catalysts as defined above, b) an activator and c) a chain transfer agent, which is able to produce hydrogenated low viscosity polyalphaolefins at high yields.

In a preferred embodiment, the activator is selected form trimethylaluminum (TMA), or triethylaluminum (TEAL), or triisobutylaluminum (TIBAL), or triisobutyl n-octylaluminum (TNOAL), or alumoxane compounds, or modified alumoxane compounds, or ionizing anion precursor, or anionic activators such as tripropylammoniumtetrakis(perfluoronaphthyl)borate.

In another preferred embodiment the chain transfer agent is selected from $H_2$, $ZnR_2$, ZnRR', $MgR_2$, MgRR', and $AlR_3$, wherein R and R' are a $C$ to $C_{10}$ alkyl group. In a more preferred embodiment, the chain transfer agent is of formula $ZnR_2$, wherein R is selected from ethyl and methyl.

A further embodiment of the present invention provides a method for the preparation of the catalyst compounds as described above, wherein the symmetric transition metal compounds may be prepared by two general synthetic routes. The parent ligands are prepared by a one-step reaction from the parent phenol or substituted phenol (Reaction A):

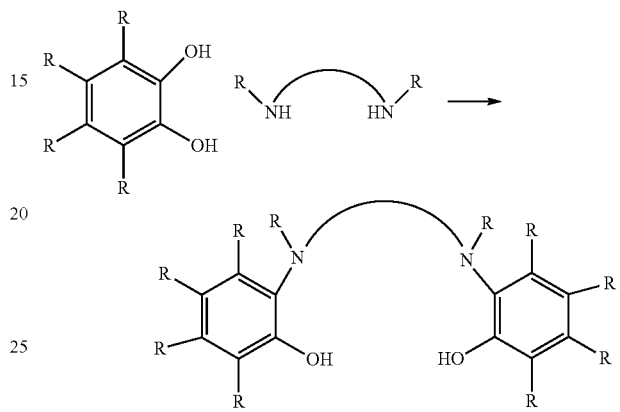

The ligand is then converted into the metal dichloride and/or alkoxide catalyst precursor by reaction with the metal tetra-functional starting material, e.g., tetrachloride, to yield the finished complex (Reaction B):

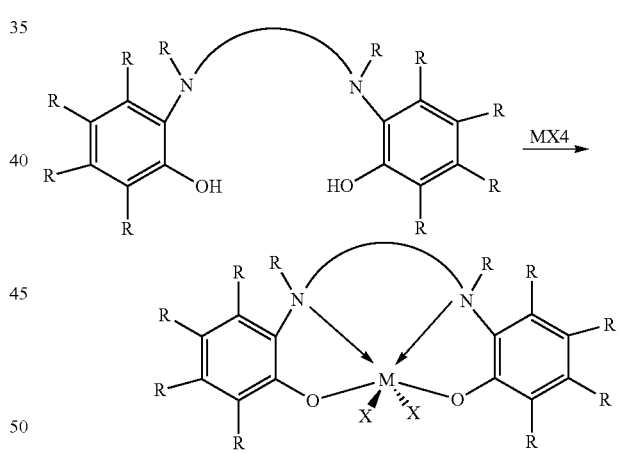

The present invention also provides a method of oligomerization process of higher olefins using the catalyst compound of the invention as described above, obtaining a polyalphaolefin and/or a polyalphaolefin-based lubricant, wherein the monomers useful herein include substituted or unsubstituted $C_4$ to $C_{14}$ alphaolefins, or $C_6$ to $C_{12}$ alphaolefins, and isomers thereof.

Therefore, in another embodiment, the invention relates to a process to produce end-saturated PAOs comprising contacting at least one olefin with a catalyst system at oligomerization conditions to produce end-saturated PAOs, the catalysts system comprising an activator, chain transfer agent, and a catalyst compound as described above.

In a preferred embodiment, the oligomerization condition comprises a temperature of from about −25° C. to about 150° C., a pressure from about 0.1 MPa to about 20 MPa, and a time period from about 5 minutes to about 36 hours.

In a preferred embodiment, the oligomerization condition comprises one or more solvents selected from isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and aromatics such as toluene, and xylene.

In another preferred embodiment, the olefin is selected from 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, and 1-docosene.

In a further embodiment of the present invention regards to the end-saturated PAOs and/or end-saturated PAOs-based lubricants obtained by the oligomerization process of the invention as described above, characterized in that the polyalphaolefin and/or polyalphaolefin-based lubricant prepared herein comprises more than 50 moles % of one or more $C_6$ to $C_{14}$ alphaolefin monomers.

The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms.

Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "polyalphaolefin" or "PAO" as used herein refers to homopolymers or copolymers of alphaolefin monomers.

In the present invention, the metal M is a metal from Group 4 selected from titanium, zirconium, hafnium, and rutherfordium, with an oxidation state selected of +3 or +4 ((although +4 is more stable). Wherein M is in an oxidation state of +3, $X_2$ in formula (I) or (Ia) is not present (absent).

In the present invention, each solid line in formulae (I) and (Ia) indicates a bond, and an arrow indicates that the bond may be dative.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings are provided by way of illustration and are not intended to be limiting of the present invention.

EXAMPLES

Example 1

Synthesize of N,N'-bis(2-hydroxy-3,5-di-tert-butylphenyl) 4,5-dimethyl-1,2-phenylenediamine, [L]

Figure 1:
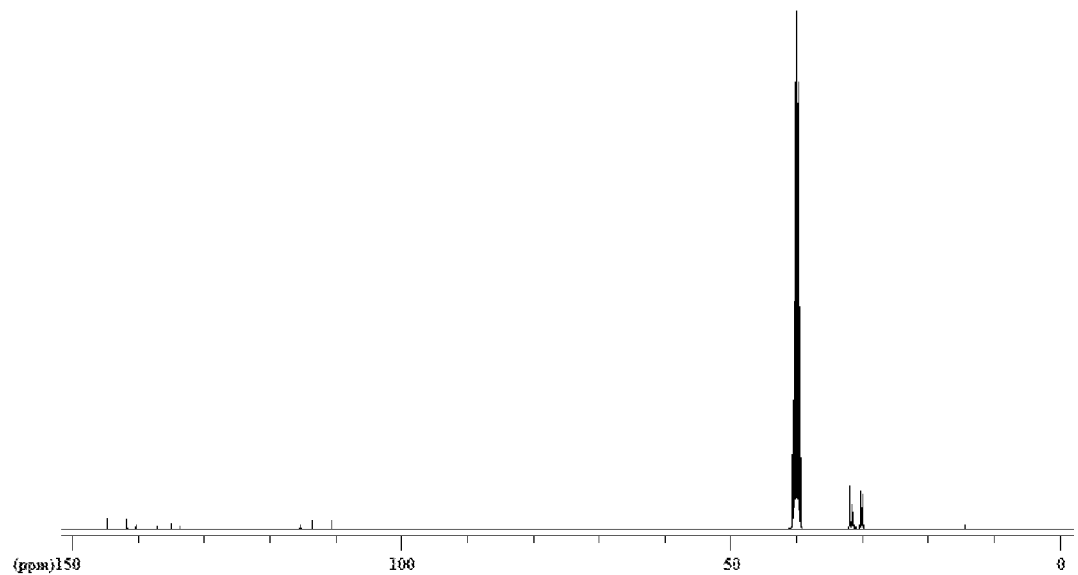
FIG. 1. $^{13}$C-NMR spectrum of N,N-bis(2-hydroxy-3,5-di-tert-butylphenyl) 4,5-dimethyl-1,2-phenylenediamine, [L].
Figure 2:
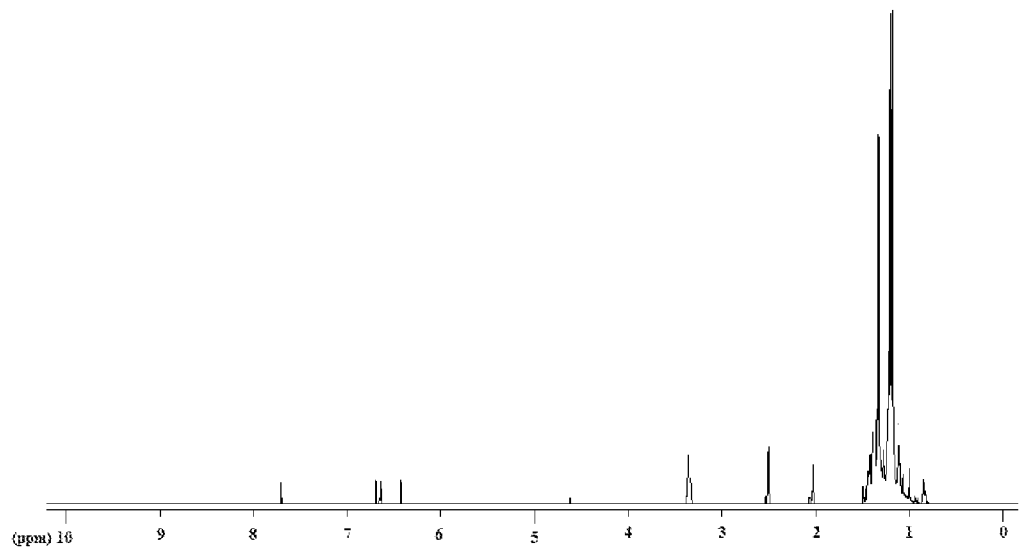
FIG. 2. $^1$H-NMR spectrum of N,N'-bis(2-hydroxy-3,5-di-tert-butylphenyl) 4,5-dimethyl-1,2-phenylenediamine, [L].

4,5-dimethyl-1,2-phenylenediamine (0.153 g; 1.125 mmol) in 2 mL acetonitrile was introduced slowly to a solution of 3,5-di-tert-butylcatechol (0.50 g; 2.25 mmol) in acetonitrile (5 mL) in the presence of air. After heating to reflux at 75° C. for 4 h, the reactor was cooled to room temperature and continued for 8 h during which time period a gray precipitate of [L] was prepared which was separated by filtration, washed three times with dried n-hexane, and air-dried. The N,N'-bis(2-hydroxy-3,5-di-tert-butylphenyl) 4,5-dimethyl-1,2-phenylenediamine, [L] was characterized by $^{13}$C-NMR spectrum (FIG. 1) and $^1$H-NMR spectrum (FIG. 2).

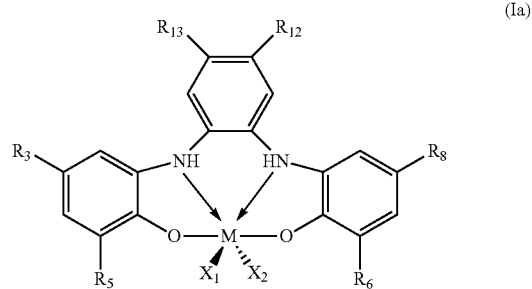

Example 2

Synthesize of [Ti{2,2'-(OC$_6$H$_{2-4}$,6-$^t$Bu$_2$)$_2$NHMePh-MeNH}(Cl$_2$], [Cat]

Figure 3:
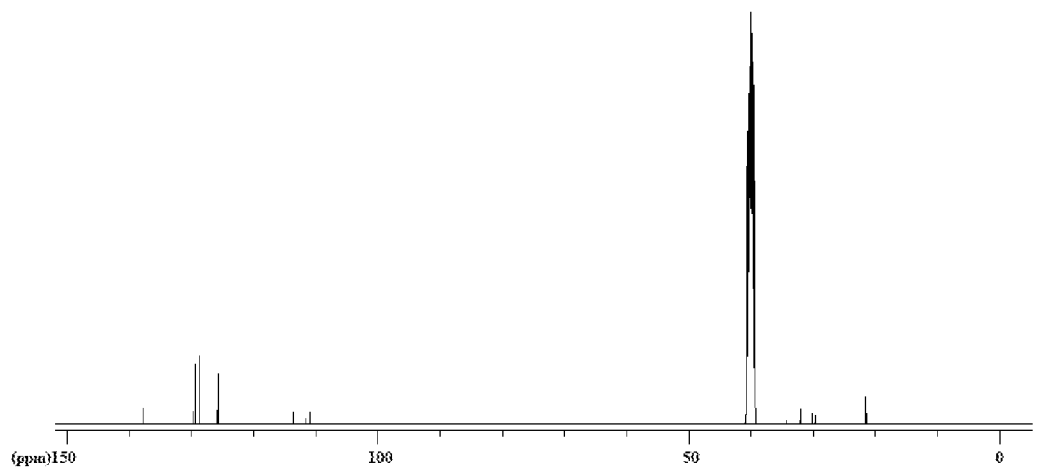
FIG. 3. $^{13}$C-NMR spectrum of [Ti{2,2'-(OC$_6$H$_2$-4,6-$^t$Bu$_2$)$_2$NHMePhMeNH}(Cl$_2$], [Cat].
Figure 4:
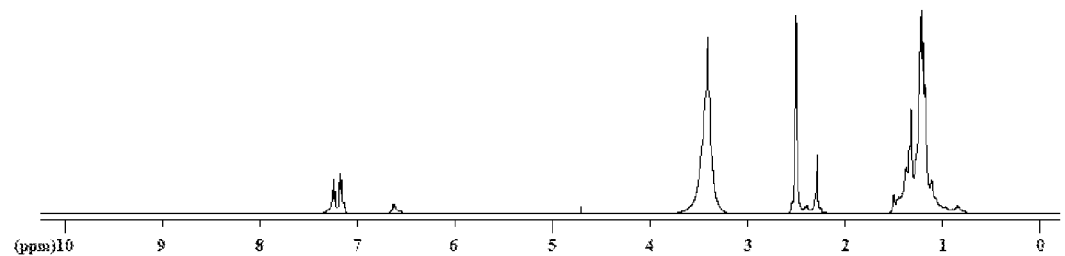
FIG. 4. $^1$H-NMR spectrum of [Ti{2,2'-(OC$_6$H$_2$-4,6-$^t$Bu$_2$)$_2$NHMePhMeNH}(Cl$_2$], [Cat].
Figure 5:
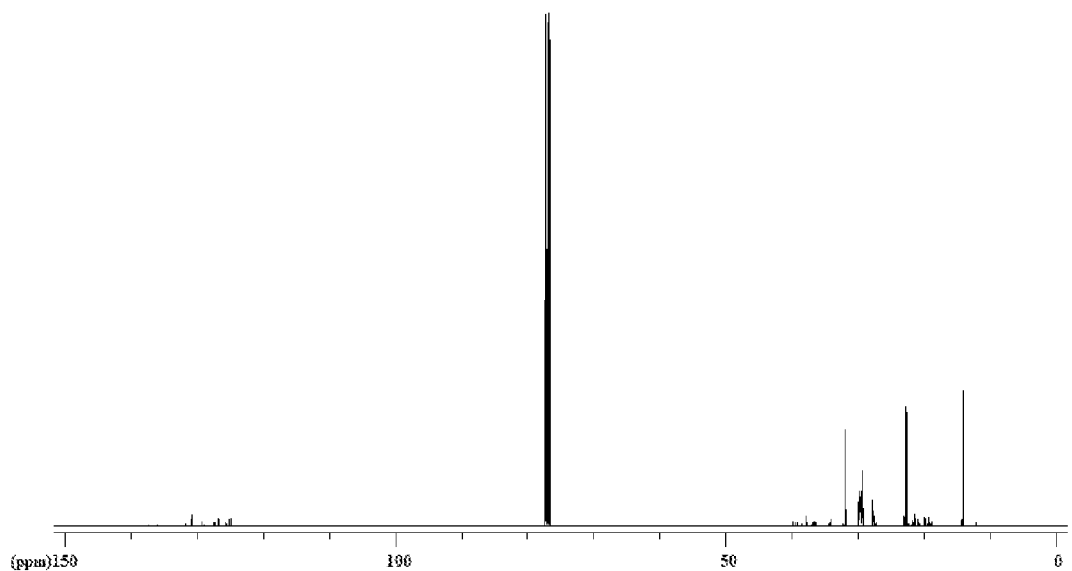
FIG. 5. $^{13}$C-NMR spectrum of prepared oligomer, Zn/Ti=0.
Figure 6:
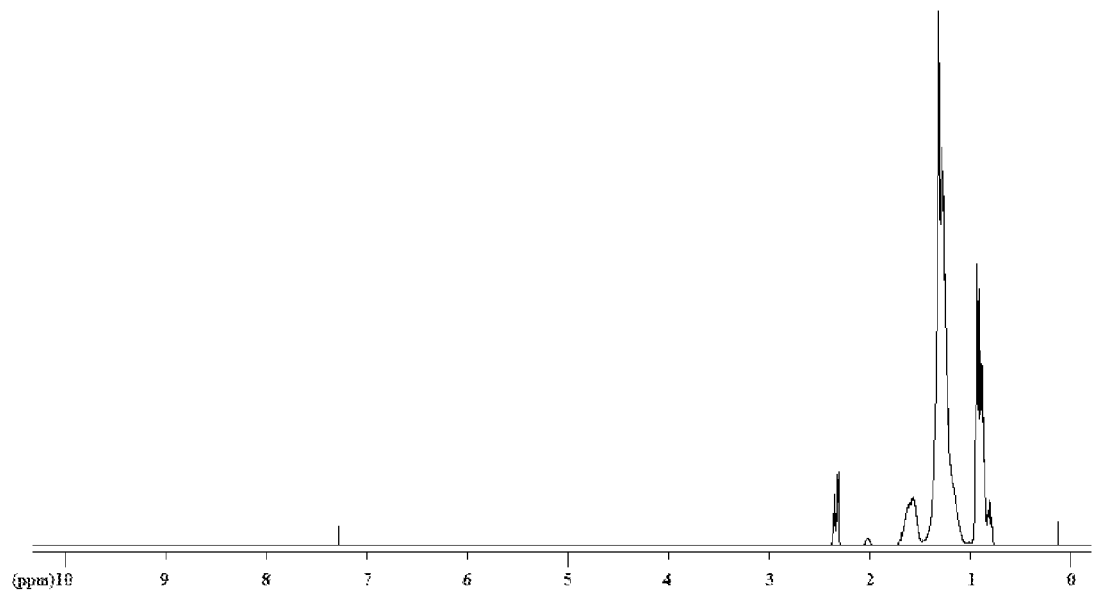
FIG. 6. $^1$H-NMR spectrum of prepared oligomer, Zn/Ti=0.
Figure 7:
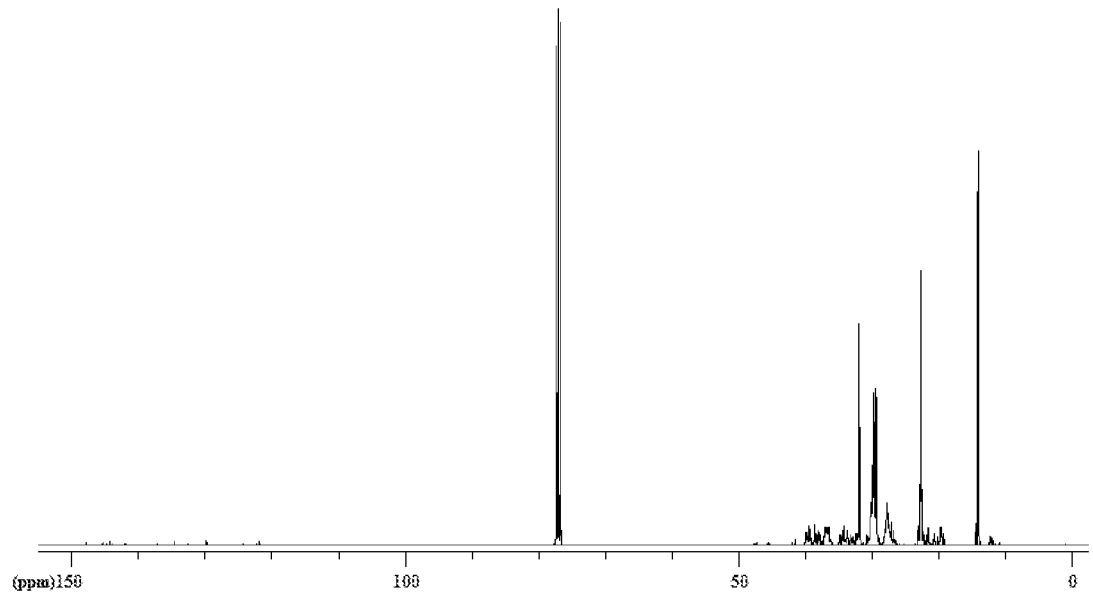
FIG. 7. $^{13}$C-NMR spectrum of prepared oligomer, Zn/Ti=30.
Figure 8:
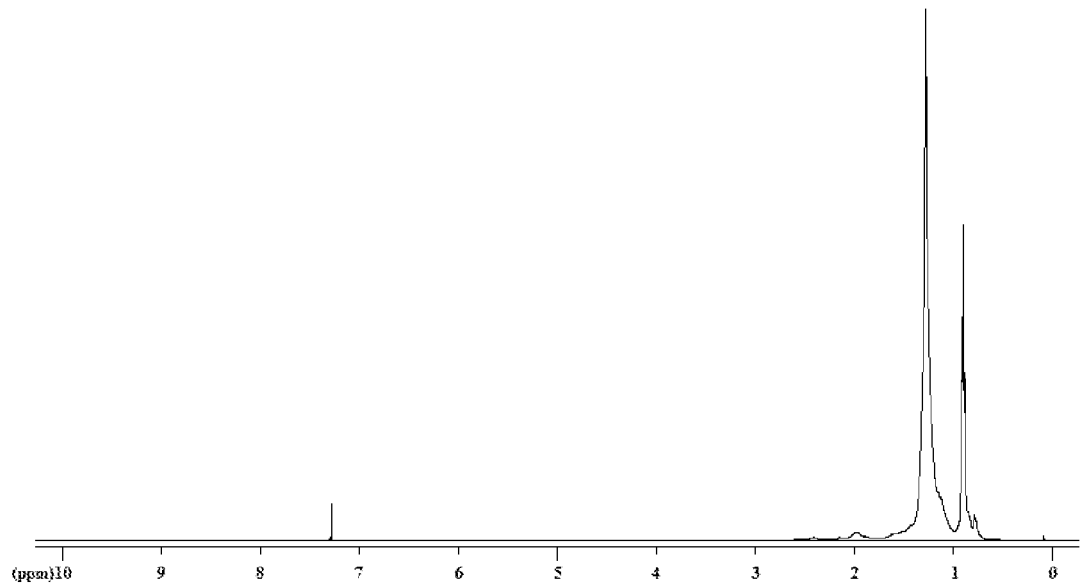
FIG. 8. $^1$H-NMR spectrum of prepared oligomer, Zn/Ti=30.
Figure 9:
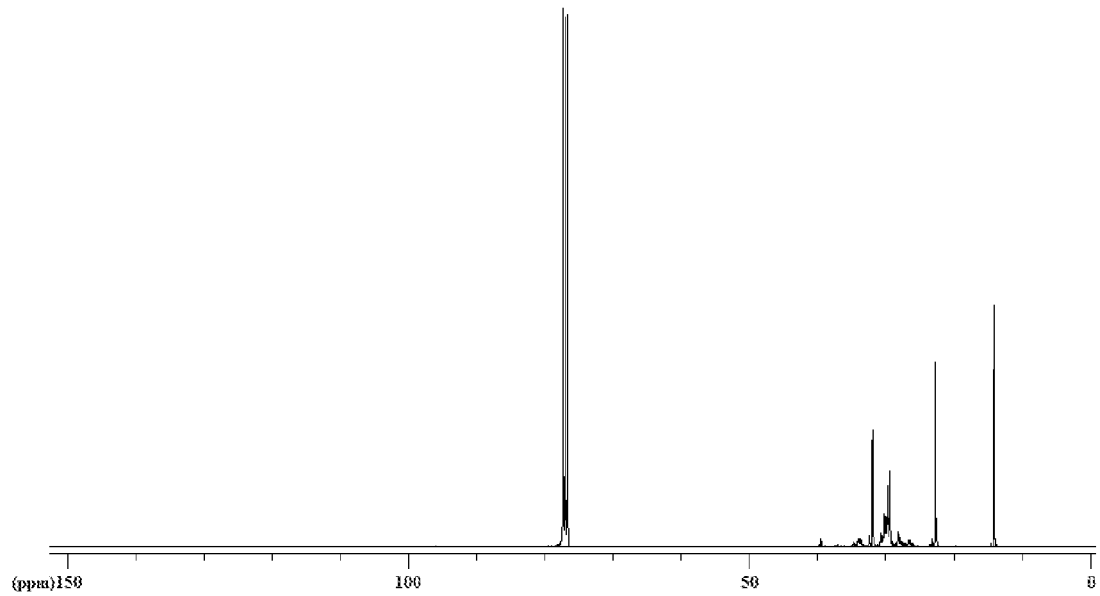
FIG. 9. $^{13}$C-NMR spectrum of prepared oligomer, Zn/Ti=90.
Figure 10:
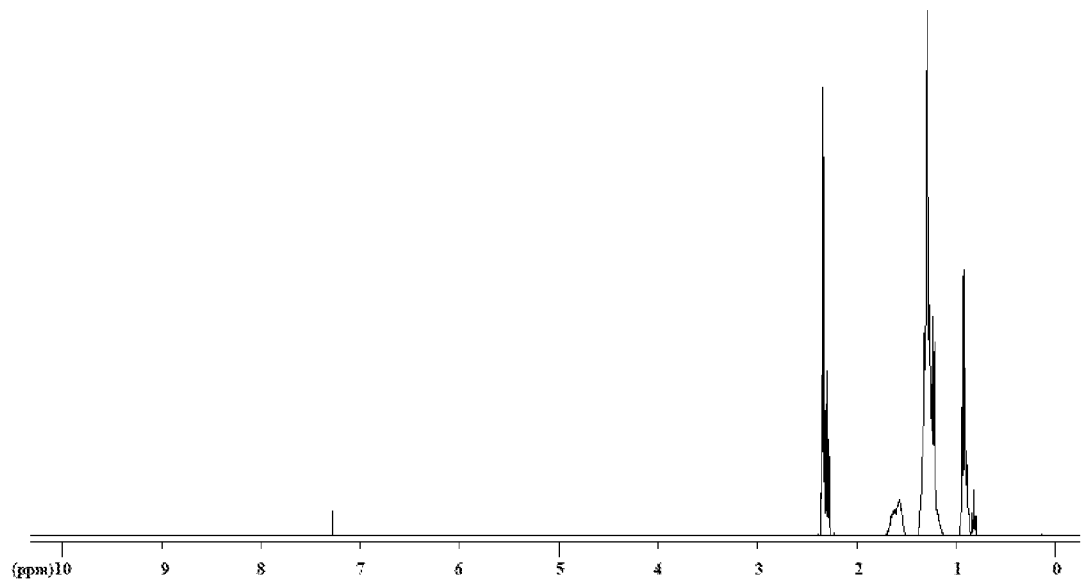
FIG. 10. $^1$H-NMR spectrum of prepared oligomer, Zn/Ti=90.
Figure 11:
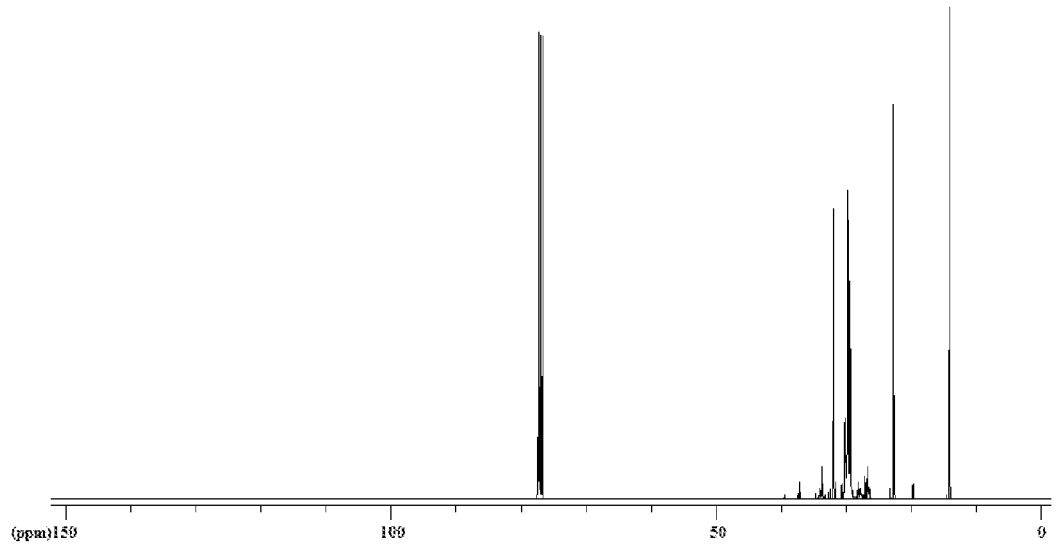
FIG. 11. $^{13}$C-NMR spectrum of prepared oligomer, Zn/Ti=120.
Figure 12:
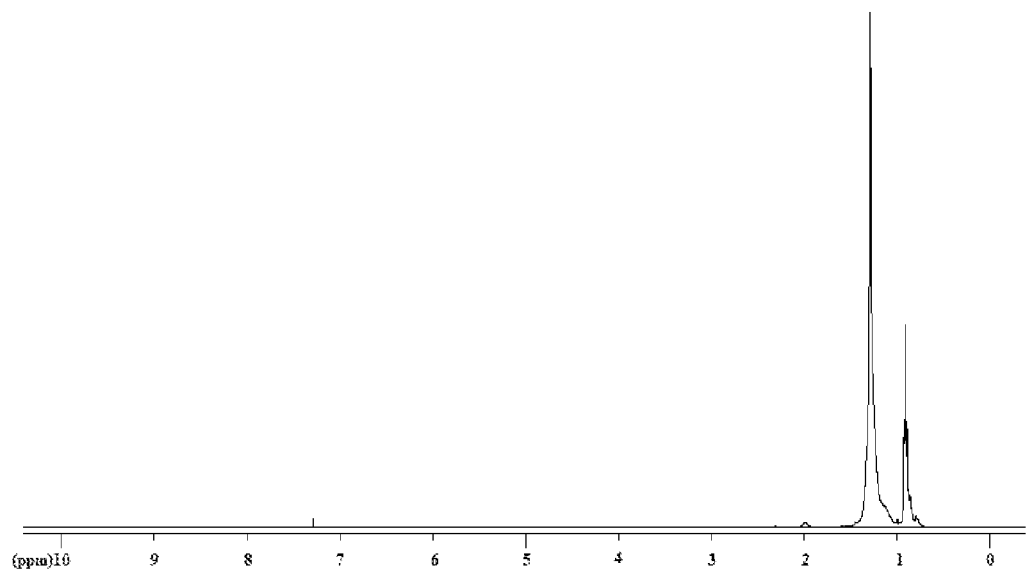
FIG. 12. $^1$H-NMR spectrum of prepared oligomer, Zn/Ti=120.

Titanium(IV) chloride (53 µL; 0.483 mmol) was added dropwise to 263 mg (0.483 mmol) of L in 5 mL of toluene at −30° C. The reactor was heated to 25° C. and stirred for a further 3 h. The solvent was removed under vacuum, and the obtained precipitate was crystallized with 10 mL of pentane. Upon standing at −30° C., a black precipitate resulted, which was filtrated and dried to give final product. The [Ti{2,2'-(OC$_6$H$_2$-4,6-$^t$Bu$_2$)$_2$NHMePhMeNH}(Cl$_2$], [Cat] was characterized by $^{13}$C-NMR spectrum (FIG. 3) and $^1$H-NMR spectrum (FIG. 4).

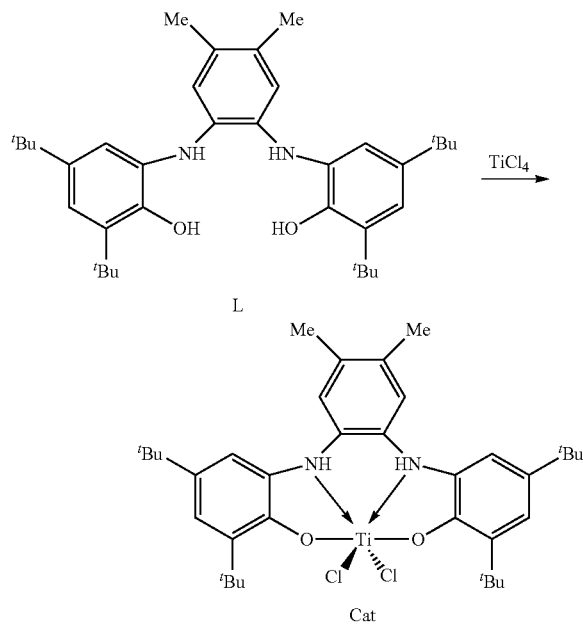

Example 3. Synthesis of Oligomerization Products

After successful synthesis of the ligand and catalyst, it was employed in the coordinative chain transfer oligomerization of 1-decene using ZnEt$_2$ as chain transfer agent and methylaluminoxane (MAO) as cocatalyst. Synthesis of 1-decene oligomers with prepared Cat and employed catalyst compound employing chain coordination transfer oligomerization (CCTO) technique:

10 mL (53 mmol) of dried 1-decene in the presence of 15 mL toluene as a solvent and appropriate amount of ZnEt$_2$ as chain transfer agent were injected into two-necked 100 mL flask. To this, 5 mL of MAO (10 wt. % in toluene, 7.56×10$^{-3}$ mol) was introduced. The oligomerization reaction was started by the injection of a 1.51×10$^{-3}$ M solution (7.56× 10$^{-6}$ mol, prepared by dissolving 0.005 g of synthesized catalyst in 5 mL of toluene) of prepared catalyst at 80° C. After 2 h, the reaction was terminated by the addition of 100 mL of a 5 wt. % HCl/methanol solution.

Obtained product was centrifuged to separate possible Zn-based solids which had been formed during the reaction. Then, the solution was washed three times with 3 wt. % solution of NaOH/H$_2$O. The unreacted monomers were extracted by high vacuum (~0.8 bar) distillation at 200° C.

This method in example was used with different chain transfer agent/catalyst ratio (mol/mol) for obtaining products 1, 2, 3, and 4 from ZnEt$_2$/Cat ratio of 0, 30, 90, and 120, respectively. Then, the products were washed and distilled to remove lights. The products had the properties given in Table 1.

TABLE 1

Results of 1-decene oligomerization at different oligomerization conditions$^a$

| Entry | Zn/Ti (mol:mol) | Time (min) | Yield (%) | Activity$^b$ | M$_n$ (g/mol) | PDI |
|---|---|---|---|---|---|---|
| 1 | 0.0 | 120 | 91.9 | 449.73 | 1162 | 1.42 |
| 2 | 30 | 120 | 86.4 | 423.28 | 938 | 1.22 |
| 3 | 90 | 120 | 79.7 | 390.21 | 630 | 1.15 |
| 4 | 120 | 120 | 74.3 | 363.75 | 525 | 1.31 |

Then, the tacticity and end unsaturation type of the synthesized oligomers were examined by $^{13}$C-NMR and $^1$H-NMR spectroscopies, respectively. The $^{13}$C-NMR and $^a$Oligomerization conditions: [Cat]=5.0 mg, 1-decene=53 mmol, Al/Ti=1000, T=80° C.;
$^b$(g oligomer)/mmol cat·h)

$^1$H-NMR spectra of prepared oligomers at Zn/Ti=0, 30, 90 and 120 are shown in FIG. 5 to FIG. 12 and the data are collected in Table 2. It was found that at Zn/Ti>90 mol/mol, unsaturation content approaches to zero. It means that at these ZnEt$_2$ contents, fully saturated PAOs are achieved.

TABLE 2

Pentad distributions and unsaturated structures in the synthesized oligomers

| Entry | Pentad distribution$^a$(%) | | | Unsaturated structures | | | |
|---|---|---|---|---|---|---|---|
| | mm | mr | rr | % Vn | % 2Vn | % 3Vn | % Vd |
| 1 | 0 | 0 | ≅100 | ≅0 | 38.2 | 53.6 | 8.2 |
| 2 | 16 | 23 | 61 | ≅0 | 31.9 | 51.3 | 16.8 |
| 3 | 27 | 41 | 32 | — | — | — | — |
| 4 | 31 | 12 | 57 | — | — | — | — |

(mm = isotactic, mr = atactic, and rr = syndiotactic).

The pour point and viscosity analyses of the resulted PAOs are gathered in Table 3. According to the results, employed CCTO technique yields PAOs with 3.5<KV$^{100}$<7.0 cSt.

TABLE 3

The pour point, viscosity and GC results of synthesized oligomers

| | Viscosity | | | GC | | | | Pour |
|---|---|---|---|---|---|---|---|---|
| Run | KV$^{100}$ (cSt) | KV$^{40}$ (cSt) | VI | % <Trimer | % Trimer | % Tetramer | % >Tetramer | point (° C.) |
| 1 | 7.9 | 46.0 | 131.7 | 6 | 5 | 35 | 54 | −48 |
| 2 | 6.8 | 37.1 | 134.5 | 4 | 6 | 36 | 54 | −55 |
| 3 | 4.2 | 17.3 | 159.7 | 3 | 57 | 28 | 12 | −50 |
| 4 | 3.5 | 13.5 | 148.7 | 9 | 52 | 31 | 8 | −59 |

To increase KV$^{100}$ of the PAO and get higher viscosity grades, oligomerization was conducted at lower temperatures of 75 and 70° C. At these oligomerization conditions, PAO6 and PAO8 were obtained with good yields, too (Table 4).

TABLE 4

Results of 1-decene oligomerization at different oligomerization conditions[a]

| Entry | T (° C.) | Zn/Ti (mol:mol) | Time (min) | Yield (%) | Activity[b] | $M_n$ (g/mol) | PDI |
|---|---|---|---|---|---|---|---|
| 5 | 75 | 90 | 120 | 76.9 | 380.92 | 855 | 1.22 |
| 6 | 70 | 90 | 120 | 74.8 | 370.51 | 1221 | 1.31 |

[a]Oligomerization conditions:
[Cat] = 5.0 mg, 1-decene = 53 mmol, Al/Ti = 1000 mol/mol; [b](g oligomer)/mmolcat.h)

The produced PAO6 and PAO8 oligomers had high VI and low pour point (Table 5) which are comparable with commercial PAO6 and PAO8.

The pour point, viscosity and GC results of synthesized oligomers

| | Viscosity | | | GC | | | | Pour |
|---|---|---|---|---|---|---|---|---|
| Run | $KV^{100}$ (cSt) | $KV^{40}$ (cSt) | VI | % <Trimer | % Trimer | % Tetramer | % >Tetramer | point (° C.) |
| 5 | 5.8 | 28.1 | 144.9 | 6 | 14 | 46 | 33 | −53 |
| 6 | 8.1 | 41.1 | 147.2 | 3 | 12 | 31 | 54 | −55 |

They also have fully saturated nature, which is beneficial for their oxidative stability.

In summary, the produced polyalphaolefins have kinematic viscosity at 100° C. ($KV^{100}$) in the range of 2-8 cSt, viscosity index (VI) above 130, and pour points in the range of −40 and −60° C. The prepared hydrocarbon lubricants can be based on either 1-decene or 1-octene monomer or even the mixture of them. The productivity of the process is at least 363.75 g of total product per mmol of transition metal and nearly 92% of monomer is converted to the PAO product in two hours.

The invention claimed is:

1. A process to produce end-saturated PAOs comprising contacting at least one olefin with a catalyst system at oligomerization conditions to produce end-saturated PAOs; wherein the catalyst system comprises a) a compound, b) an activator, and c) a chain transfer agent with formula $ZnR_2$, wherein R is selected from ethyl and methyl; wherein that compound is of formula (I):

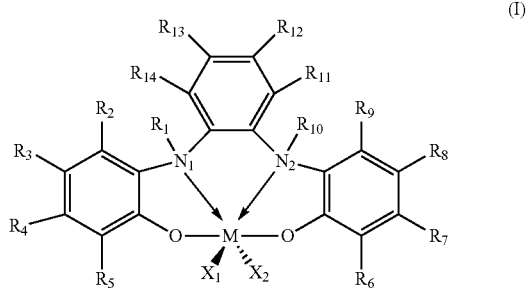

wherein $X_1$ and $X_2$ are independently selected from a $C_1$ to $C_{20}$ hydrocarbyl radical and halogen, or $X_1$ and $X_2$ join together to form a $C_4$ to $C_{12}$ cyclic or polycyclic ring structure, provided, $R_1$, $R_2$, $R_4$, $R_7$, $R_9$, $R_{10}$, $R_{11}$, $R_{12}$, $R_{13}$, and $R_{14}$ are independently selected from a hydrogen and a $C_1$ to $C_{10}$ hydrocarbyl group;
wherein $R_3$, $R_5$, $R_6$, and $R_8$ are independently a $C_1$ to $C_{40}$ hydrocarbyl group; and
wherein the activator is an alumoxane compound or tripropylammoniumtetrakis(perfluoronaphthyl)borate.

2. The process of claim 1, wherein the oligomerization condition comprises a temperature of from about −25° C. to about 150° C., a pressure from about 0.1 MPa to about 20 MPa, and a time period from about 5 minutes to about 36 hours.

3. The process of claim 1, wherein the oligomerization condition comprises one or more solvents selected from isobutane, butane, pentane, isopentane, hexanes, isohexane, heptane, octane, dodecane, and mixtures thereof; cyclic and alicyclic hydrocarbons, and aromatics.

4. The process of claim 1, wherein the olefin is selected from 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, and 1-docosene.

* * * * *

UNITED STATES PATENT AND TRADEMARK OFFICE
CERTIFICATE OF CORRECTION

| | |
|---|---|
| PATENT NO. | : 11,505,626 B2 |
| APPLICATION NO. | : 17/217493 |
| DATED | : November 22, 2022 |
| INVENTOR(S) | : Ahad Hanifpour et al. |

It is certified that error appears in the above-identified patent and that said Letters Patent is hereby corrected as shown below:

In the Claims

Column 10, Claim 1, Line 15, after Formula (I), insert -- wherein M is selected from titanium, zirconium, hafnium, and rutherfordium; --.

Signed and Sealed this
First Day of August, 2023

Katherine Kelly Vidal
*Director of the United States Patent and Trademark Office*